(12) United States Patent
Hatsuda

(10) Patent No.: US 7,898,381 B2
(45) Date of Patent: Mar. 1, 2011

(54) SENSOR SHEET

(75) Inventor: Masahiro Hatsuda, Yamatokoriyama (JP)

(73) Assignee: Nitta Corporation, Osaka-shi (JP)

( * ) Notice: Subject to any disclaimer, the term of this patent is extended or adjusted under 35 U.S.C. 154(b) by 0 days.

(21) Appl. No.: 12/452,086

(22) PCT Filed: Jul. 3, 2008

(86) PCT No.: PCT/JP2008/062049

§ 371 (c)(1),
(2), (4) Date: Dec. 15, 2009

(87) PCT Pub. No.: WO2009/013981

PCT Pub. Date: Jan. 29, 2009

(65) Prior Publication Data

US 2010/0134236 A1    Jun. 3, 2010

(30) Foreign Application Priority Data

Jul. 26, 2007   (JP) .............................. 2007-194408

(51) Int. Cl.
*H01C 10/10* (2006.01)
(52) U.S. Cl. ......................... 338/47; 338/334; 338/114
(58) Field of Classification Search .................. 338/47, 338/13, 202, 206, 322, 333, 334, 114
See application file for complete search history.

(56) References Cited

U.S. PATENT DOCUMENTS

| | | | |
|---|---|---|---|
| 6,531,951 B2 * | 3/2003 | Serban et al. | 338/47 |
| 7,068,142 B2 * | 6/2006 | Watanabe et al. | 338/47 |
| 7,262,682 B2 * | 8/2007 | Ooba et al. | 338/2 |

FOREIGN PATENT DOCUMENTS

| | | |
|---|---|---|
| JP | A-2001-255221 | 9/2001 |
| JP | A-2004-28883 | 1/2004 |

(Continued)

OTHER PUBLICATIONS

International Search Report mailed on Aug. 5, 2008 in corresponding International Application No. PCT/JP2008/062049.

*Primary Examiner*—Kyung Lee
(74) *Attorney, Agent, or Firm*—Oliff & Berridge, PLC

(57) ABSTRACT

The body pressure distribution sensor sheet includes a first sheet, a second sheet, and a plurality of pressure-sensitive regions interposing between the first sheet and the second sheet. The pressure-sensitive regions are arranged in two directions, i.e., a lengthwise direction and a transverse direction to form a matrix. A first opening, a second opening, and a cut line are formed in an area between a pair of pressure-sensitive regions and adjacent to each other in a first oblique direction. The shape of the first opening is defined by a plurality of borders including a border and a border. The border extends from one end of the cut line in the transverse direction, and the border extends from the one end of the cut line in the lengthwise direction. The shape of the second opening is defined by a plurality of borders including a border and a border. The border extends from the other end of the cut line in the transverse direction, and the border extends from the other end of the cut line in the lengthwise direction.

7 Claims, 13 Drawing Sheets

FOREIGN PATENT DOCUMENTS

| | | |
|---|---|---|
| JP | A-2004-264172 | 9/2004 |
| JP | A-2004-333273 | 11/2004 |
| JP | A-2006-90983 | 4/2006 |
| JP | A-2007-517216 | 6/2007 |
| JP | A-2007-199006 | 8/2007 |
| WO | WO 2005/068961 A1 | 7/2005 |

* cited by examiner

FIG.2
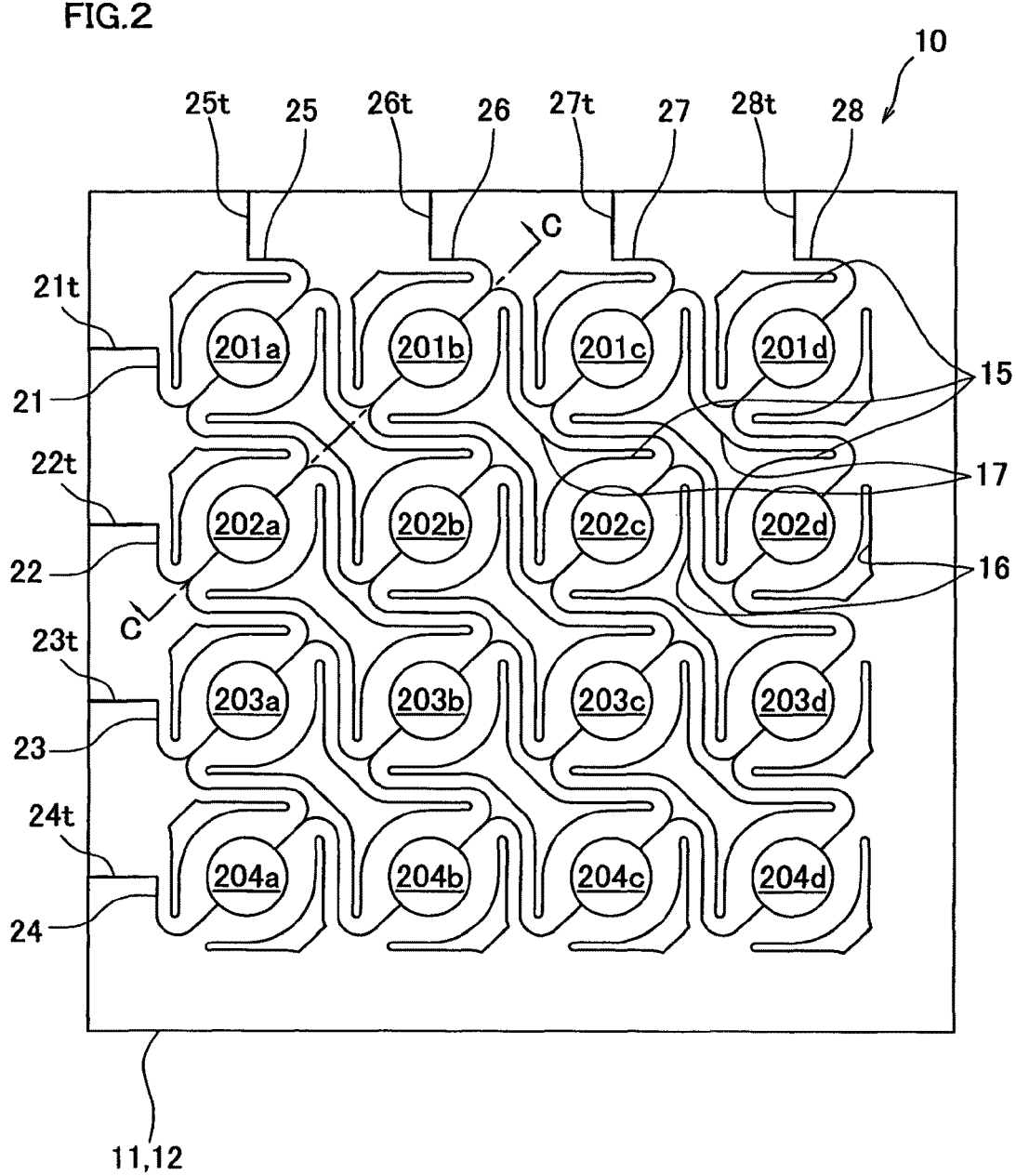
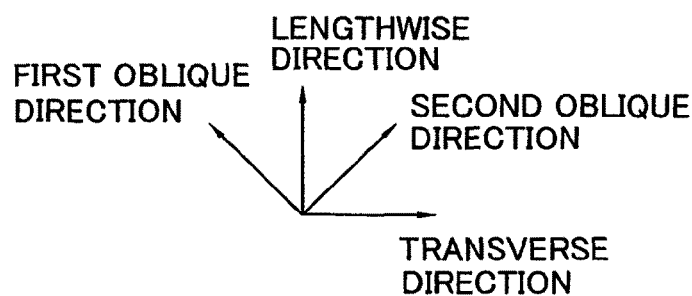

FIG.4
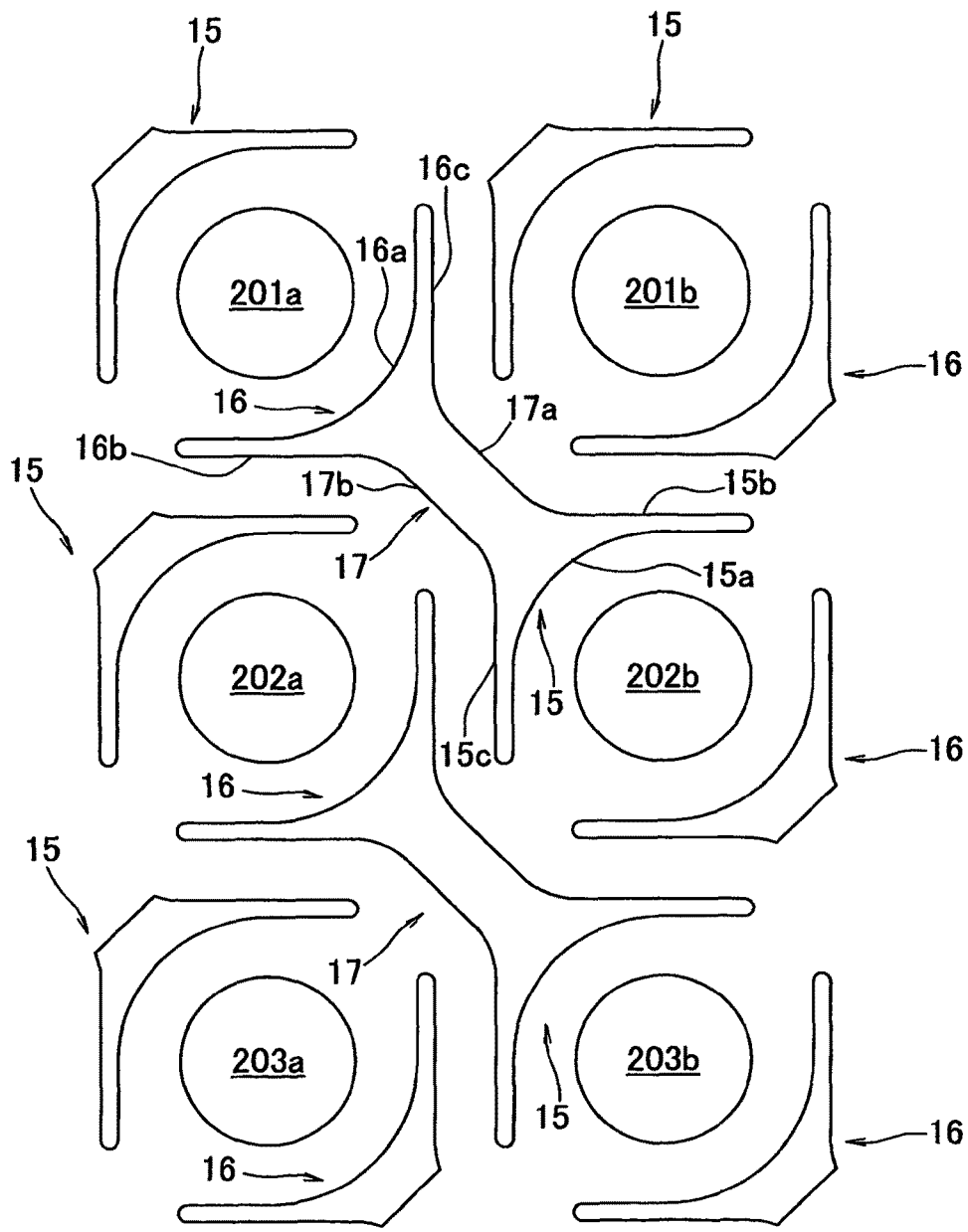
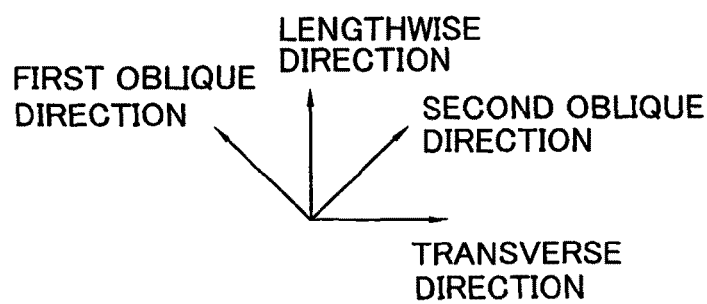

FIG. 6
(a) TRANSVERSE DIRECTION
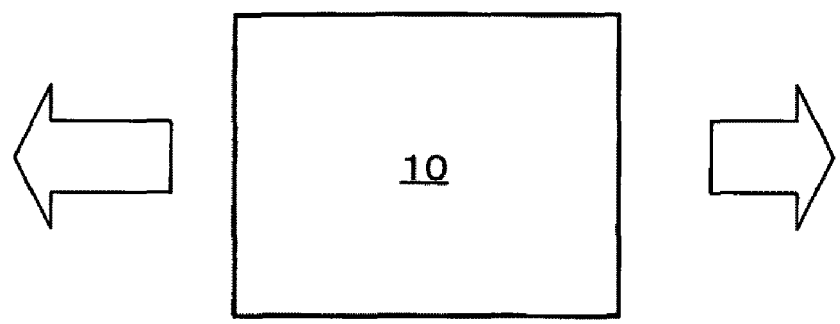
(b) LENGTHWISE DIRECTION
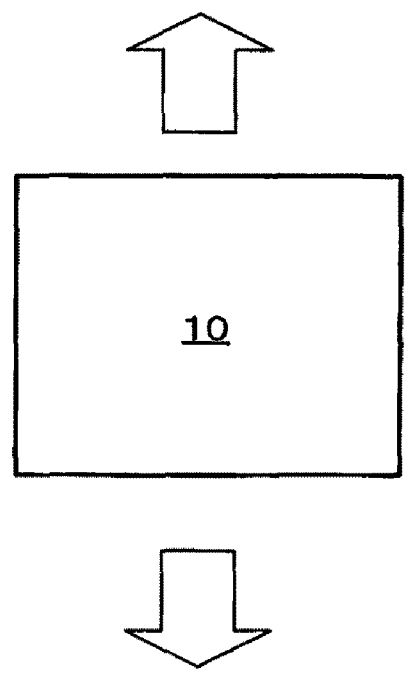

FIG.11
(a)
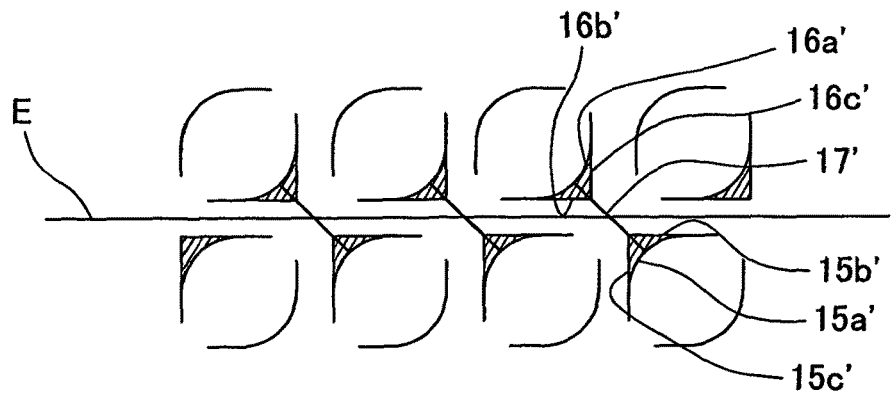
(b)
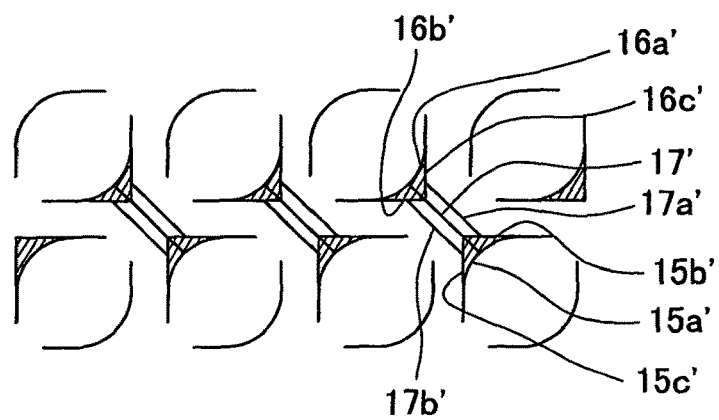
(c)
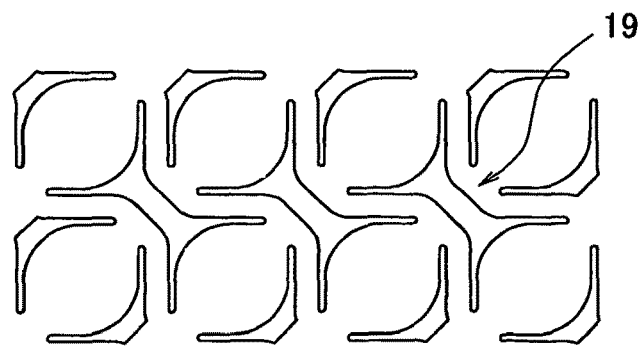

180; # SENSOR SHEET

TECHNICAL FIELD

The present invention relates to a sensor sheet utilized for measuring distribution of pressure on a predetermined area of the sensor sheet.

BACKGROUND ART

Patent Document 1 discloses a pressure distribution measurement sensor sheet having a sheet area where a plurality of rectangular electrodes are vertically aligned in a horizontal orientation, and another sheet area where a plurality of rectangular electrodes are horizontally aligned in a vertical orientation. A pressure-sensitive layer is provided on the electrodes of each of the two sheets. The two sheets are laminated in such a manner that the pressure-sensitive layer of each of the sheets contacts each other to constitute a pressure distribution measurement sensor sheet. In the sensor sheet, the rectangular electrodes arranged in each of the sheet areas intersect one another. Each of the intersections functions as a pressure-sensitive region to realize a pressure distribution sensor having a matrix structure. Pressure distribution measurement is possible in the sensor sheet by sequentially energizing the electrodes and measuring electric resistance between the electrodes.

The sensor sheet of Patent Document 1 is capable of properly measuring pressure distribution when disposed on a plane surface; however, when disposed on a flexible support such as mattress or futon mattress, the sensor sheet is not capable of deforming to conform to unevenness of a surface of the support. This prevents the sensor sheet from properly measuring pressure distribution. A conceivable approach to solving the problem is adopting a stretchable material such as vinyl chloride or ethyl carbonate as a substrate. Such a case requires wires formed by applying ink on the substrate to be stretched as well in accordance with the sensor sheet. Nonetheless, it is difficult to give stretchability to the sensor sheet while maintaining the electrical properties of the wires. Further, although the ink needs to be dry to cure when forming a wire, having stretchability makes it difficult for the ink to do so.

As a solution to the above problem, Patent Document 2 discloses a body pressure distribution sensor sheet having stretchability. In the sensor sheet, a plurality of electrodes having pressure-sensitive resistors laminated thereon are arranged apart from one another to form a matrix, and adjacent electrodes are connected by a wire. Further, around each of the electrodes on the sensor sheet is a spiral cut line formed without intersecting with the wire, enabling the entire sheet to stretch.

Patent Document 1: Tokukai 2004-333273 (Japanese Unexamined Patent Publication)

Patent Document 2: WO-A1-2005068961

DISCLOSURE OF THE INVENTION

Problems to be Solved by the Invention

A sensor sheet having a spiral cut line, however, brings up such problems as described below.

First, while the sensor sheet having a spiral cut line stretches well in a lengthwise direction, the sensor sheet barely stretches in a transverse direction; i.e., direction perpendicular to the lengthwise direction. Thus, the sensor sheet is not capable of properly measuring pressure distribution when disposed on a flexible support such as mattress or futon mattress.

Further, when a cut line formed on the sensor sheet is spiral, the length of the cut-line is excessively long. Here, if a cut line is formed by laser beam machining during manufacturing of the sensor sheet, a longer cut line requires a longer exposure time than a shorter cut line. This elongates the time it takes to form a spiral cut line, thus increasing a production cost. Furthermore, when a cut line is stamped out by pressing during the manufacture of a sensor sheet, repeating partial stamping is necessary. Thus, a longer cut line requires more stamping than a shorter cut line. This elongates the time it takes to form a spiral cut line, thus increasing a production cost.

Further, a spiral cut line requires a spiral wire which connects electrodes. This excessively elongates the wire, which also increases the production cost.

Thus, an object of the present invention is to provide a sensor sheet capable of properly measuring pressure distribution even when disposed on a flexible support.

Another object of the present invention is to provide a sensor sheet whose opening and cut line are speedily formed at a low cost.

Technique for Solving the Problems

The sensor sheet of the present invention includes a first sheet, a second sheet, and a plurality of pressure-sensitive resistors. The first sheet has a plurality of electrodes arranged apart from each other thereon in two directions, i.e., a lengthwise direction and a transverse direction to form a matrix. The second sheet, which is laminated on to the first sheet, has a plurality of electrodes arranged apart from each other thereon in the two directions to form a matrix in such a manner that the electrodes respectively face the electrodes of the first sheet. An electrode of the first sheet and an electrode of the second sheet sandwich a pressure-sensitive resistor. A first opening, a second opening, and a cut line are formed between each pair of electrodes adjacent in one oblique direction, i.e., direction between the lengthwise direction and the transverse direction. The first opening is formed between the pair of electrodes and near a first electrode of the pair of electrodes. The second opening is formed between the first opening and a second electrode of the pair of electrodes, and near the second electrode. The cut line formed with a pair of borders extending in the one oblique direction connects the first opening and the second opening. The first opening is defined by a plurality of borders including a first border and a second border. The first border is connected to a first one of the pair of borders of the cut line, and extends in the transverse direction. The second border is connected to a second one of the pair of borders which form the cut line, and extends in the lengthwise direction. The second opening is defined by a plurality of borders including a third border and a fourth border. The third border is connected to the second one of the pair of borders of the cut line, and extends in the transverse direction. The fourth border is connected to the first one of the pair of borders of the cut line, and extends in the lengthwise direction.

Note that a cut line in the present invention includes an opening having a relatively small constant width.

According to the present invention, first and second openings and a cut line allow the sensor sheet to stretch in lengthwise and transverse directions. This enables the sensor sheet to deform while conforming to an uneven surface of a support, even when disposed on a flexible support such as mattress or futon mattress. Thus, pressure distribution is properly measured.

Further, a total length of the lengths of outlines of the first and second openings and the length of the outline of the cut line is shorter than the length of a spiral cut line. Thus, the first and second openings and the cut lines are speedily formed at a low cost.

Preferably, the first opening is defined by the first border, the second border, and a fifth border which curves to project towards the second electrode. Also, the second opening is preferably defined by the third border, the fourth border, and a sixth border which curves to project towards the first electrode. Thus, stretchability of the sensor sheet in lengthwise and transverse directions is improved with a simple structure.

Here, each of the electrodes may be circular. The fifth border may have a portion formed along an outline which is a quarter-circle around the first electrode, the quarter-circle outline facing the second electrode. The sixth border may have a portion formed along an outline which is a quarter-circle around the second electrode, the quarter-circle outline facing the first electrode. This allows the sensor sheet to improve its stretchability in lengthwise and transverse directions, while preventing the openings from intersecting each other.

Preferably, the cut line is formed between a center portion of the first opening and a center portion of the second opening. This equalizes the stretchability in the lengthwise direction and the transverse direction.

Preferably, the pair of borders which form the cut line are apart from one another. This keeps the pair of borders forming the cut line from contacting one another even when the sensor sheet is bent along the one oblique direction. Thus, the pair of borders are not interfered with one another by contacting one another. This realizes proper measurement of pressure distribution.

The first sheet has a wire connecting the electrodes formed thereon, and the second sheet has wires connecting the electrodes formed thereon. Preferably, the wire on the first sheet and the wire on the second sheet are both provided avoiding the first opening and the second opening. Thus, measurement of pressure distribution is realized without losing the stretchability of the sensor sheet in the lengthwise and transverse directions.

It is preferred that: the first border and the first one of the pair of borders of the cut line are smoothly connected; the second border and the second one of the pair of borders of the cut line are smoothly connected; the third border and the second one of the pair of borders of the cut line are smoothly connected; and the fourth border and the first one of the pair of borders of the cut line are smoothly connected. Thus, the vicinity of the connection between the first or the second opening and the cut line is less likely to partially project from the surface of the sensor sheet when the sensor sheet is bent in either the lengthwise direction or the transverse direction. Thus, proper measurement of pressure distribution is realized even when the sensor sheet is deformed to bend.

EFFECT OF THE INVENTION

According to the present invention, the sensor sheet is capable of deforming while conforming to an uneven surface of a flexible support. This realizes proper measurement of pressure distribution. In addition, the first and second openings and the cut line are speedily formed at a low cost.

BRIEF DESCRIPTION OF THE DRAWINGS

FIG. 2 is an external view of the body pressure distribution sensor sheet of FIG. 1.

FIG. 4 is a magnified view of a main part of FIG. 2 without the wires.

FIG. 6 is a schematic view illustrating stretchability of the body pressure distribution sensor sheet in a transverse direction and a lengthwise direction.

FIG. 11 illustrates a method of forming first and second openings and cut lines of a body pressure distribution sensor sheet, in sequence of processes.

Figure 1:
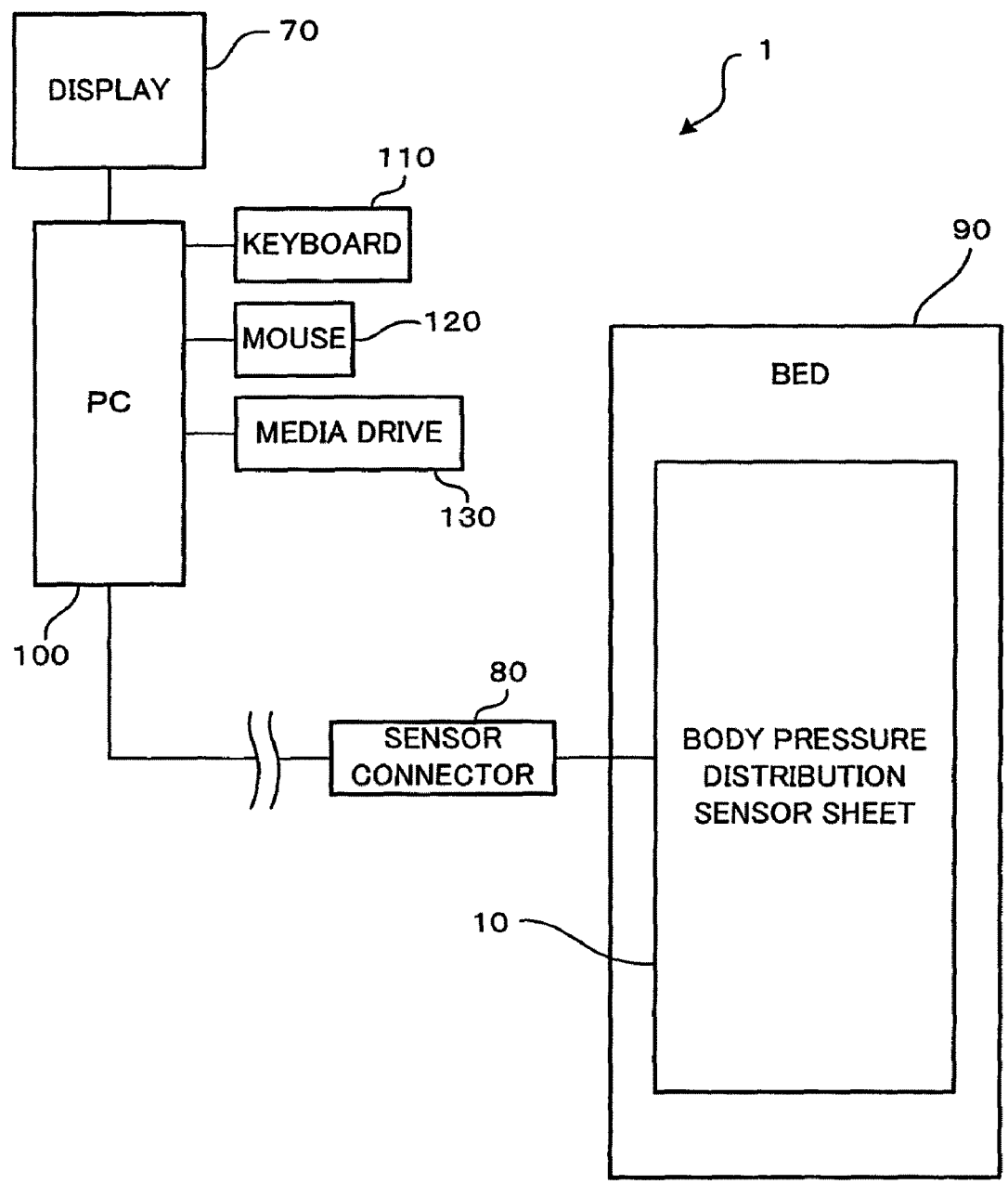
FIG. 1 is an overall view of a body pressure distribution measurement system of an embodiment of the present invention.

| REFERENCE NUMERALS | |
|---|---|
| 1 | BODY PRESSURE DISTRIBUTION MEASUREMENT SYSTEM |
| 10 | BODY PRESSURE DISTRIBUTION SENSOR SHEET |
| 11 | FIRST SHEET |
| 12 | SECOND SHEET |
| 15 | FIRST OPENING |
| 15A | BORDER (FIFTH BORDER) |
| 15B | BORDER (FIRST BORDER) |
| 15C | BORDER (SECOND BORDER) |
| 16 | SECOND OPENING |
| 16A | BORDER (SIXTH BORDER) |
| 16B | BORDER (THIRD BORDER) |
| 16C | BORDER (FOURTH BORDER) |
| 17 | CUT LINE |
| 17A, 17B | BORDER |
| 21 TO 28 | WIRE |
| 21T TO 28T | ELECTRIC TERMINAL |
| 31A TO 31D, 32A TO 32D, 33A TO 33D, 34A TO 34D, 41A TO 41D, 42A TO 42D, 43A TO 43D, 44A TO 44D | ELECTRODE |
| 51A TO 51D, 52A TO 52D, 53A TO 53D, 54A TO 54D, 61A TO 61D, 62A TO 62D, 63A TO 63D, 64A TO 64D | PRESSURE-SENSITIVE RESISTOR |
| 201A TO 201D, 202A TO 202D, 203A TO 203D | PRESSURE-SENSITIVE REGION |

BEST MODE FOR CARRYING OUT THE INVENTION

The following describes a preferable embodiment of the present invention, with reference to the figures.

Here, an embodiment is described where a sensor sheet according to the present invention is installed as a body pressure distribution sensor sheet which is a part of a body pressure distribution measurement system. FIG. 1 is an overall view of a body pressure distribution measurement system of an embodiment of the present invention.

A body pressure distribution measurement system 1 includes a PC (personal computer) 100, a display 70, a bed 90, a sensor connector 80, and a body pressure distribution sensor sheet 10. The body pressure distribution sensor sheet 10 is provided to an upper surface of a mattress of the bet 90, and is connected to the PC 100 via the sensor connector 80. The system is used with a patient (not shown) lying on the body pressure distribution sensor sheet 10. The system is utilized for monitoring part of the patient's body where a pressure sore is likely to develop, by measuring body pressure when the patient is lying on the bed.

The body pressure distribution measurement system 1 is capable of monitoring body pressure distribution on a patient by operating the PC 100 with a keyboard 100 and/or a mouse 120. In the body pressure distribution measurement system 1, body pressure measurement data measured by the body pressure distribution sensor 10 is sent to the PC 100, and the body pressure distribution measurement result is displayed on the display 70.

Further, the body pressure distribution measurement system 1 is capable of remotely monitoring body pressure distribution on a patient with the PC 100, when the bed 90 is provided apart from the PC 100.

Figure 3:
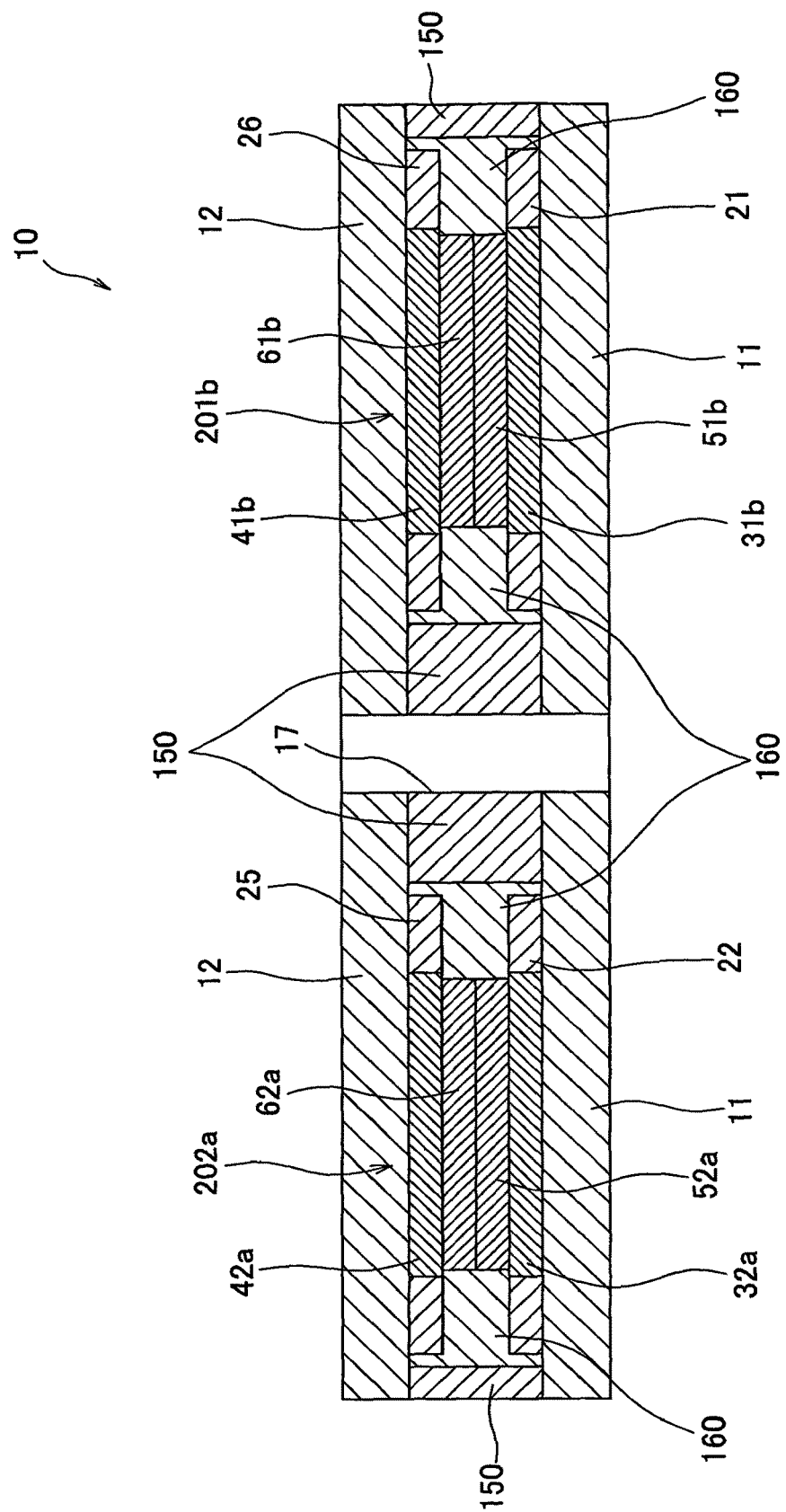
FIG. 3 is a cross-sectional view taken along the C-C line of FIG. 2.
Figure 5:
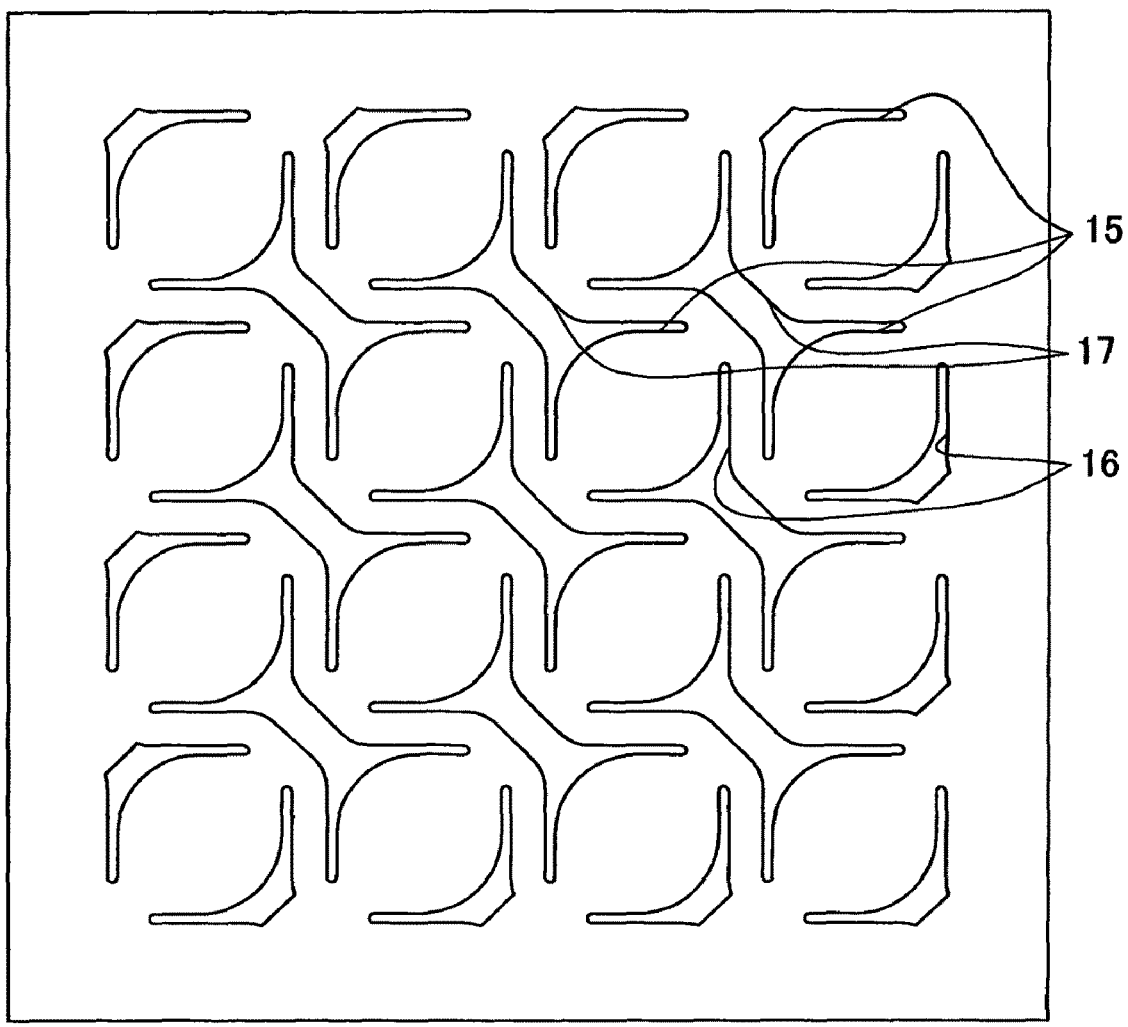
FIG. 5 illustrates shapes of the first and second openings and cut lines of the body pressure distribution sensor sheet of FIG. 2.

Next, the following describes a structure of the body pressure distribution sensor sheet 10, with reference to FIGS. 2 to 5. FIG. 2 is an external view of the body pressure distribution sensor sheet of FIG. 1. FIG. 3 is a cross-sectional view taken along the C-C line of FIG. 2. FIG. 5 illustrates shapes of the first and second openings and the cut lines of the body pressure distribution sensor sheet of FIG. 2.

The following describes an overall structure of the body pressure distribution sensor sheet 10. As illustrated in FIG. 2, the body pressure distribution sensor sheet 10 includes: a first sheet 11; a second sheet 12; a plurality of circular pressure-sensitive regions 201a to 201d, 202a to 202d, 203a to 203d, and 204a to 204d; column wires 21 to 24; and row wires 25 to 28. Further, the body pressure distribution sensor sheet 10 has a plurality of first openings 15, a plurality of second openings 16, and a plurality of cut lines 17 formed thereon. The cut lines 17 are substantial openings in the present embodiment. The pressure-sensitive regions 201a to 201d, 202a to 202d, 203a to 203d, and 204a to 204d are apart from each other and arranged in a lengthwise direction (up/down direction in FIG. 2) and a transverse direction (left/right direction in FIG. 2) to form a matrix.

Next, the following describes a structure of each of the pressure-sensitive regions. Only structures of the two pressure-sensitive regions 202a and 201b are described here; however, other pressure-sensitive regions have the same structure. The pressure-sensitive region 202a includes an electrode 32a on the first sheet 11; pressure-sensitive resistor 52a formed on the electrode 32a; an electrode 42a on the second sheet 12; and a pressure-sensitive resistor 62a formed on the electrode 42a, as illustrated in FIG. 3. Likewise, the pressure-sensitive regions 201b includes: an electrode 31b on the first sheet 11; a pressure-sensitive resistor 51b formed on the electrode 31b; an electrode 41b on the second sheet 12; and a pressure-sensitive resistor 61b formed on the electrode 41b.

Here, each of the pressure-sensitive resistors is dry-solidified pressure-sensitive conductive ink. The pressure-sensitive conductive ink has such nature that its electric resistance changes according to the pressure applied.

Next, the following describes the first opening 15, the second opening 16, and the cut line 17 of the body pressure distribution sensor sheet 10. FIG. 4 illustrates the pressure-sensitive regions 201a, 201b, 202a, 202b, 203a, and 203b of the body pressure distribution sensor sheet 10. The following description takes as an example the first opening 15 and the second opening 16 formed between the pressure-sensitive regions 201a and 202b, and the cut line 17 which connects the first opening 15 and the second opening 16. Further, a pair of pressure-sensitive regions adjacent to one another in a first oblique direction, i.e., direction from the upper left to the lower right in FIG. 2 has a first opening 15, a second opening 16, and a cut line 17 formed therebetween.

Formed between the pair of pressure-sensitive regions 201a and 202b adjacent to one another in the first oblique direction from the upper left to the lower right is a substantially L-shaped first opening 15, as illustrated in FIG. 4. The perpendicular corner of the substantial L shape of the first opening 15 is on a line segment connecting a center portion of the pressure-sensitive region 201b and a center portion of the pressure-sensitive region 201a. The first opening 15 is provided near the pressure-sensitive regions 202b between the pressure-sensitive regions 202b and 201a (between the pressure-sensitive region 202b and each of the pressure sensitive regions 201a, 201b, and 202a, to be more specific).

Further, formed between the pair of pressure-sensitive regions 201a and 202b is a substantially L-shaped second opening 16. The perpendicular corner of the substantial L shape of the second opening 16 is positioned on a line segment connecting a center portion of the pressure-sensitive region 202a and the pressure-sensitive region 202b. The second opening 16 is near the pressure-sensitive region 201a between the first opening 15 and the pressure-sensitive region 201a.

Further, between the pair of pressure-sensitive regions 201a and 202b is a cut line 17 connecting the first opening 15 and the second opening 16. The cut line 17 is formed with a pair of borders 17a and 17b each extending in the first oblique direction. In the present embodiment, the pair of borders 17a and 17b are located with a distance therebetween, the distance being equal to or shorter than the diameter of the pressure-sensitive region 201a. The cut line 17 is actually an opening long in the first oblique direction, as described above. The cut line 17 is formed between a center portion of the first opening 15 and a center portion of the second opening 16. The first opening 15, the second opening 16, and the cut line 17 are holes formed by pressing or laser beam machining to penetrate the body pressure distribution sensor sheet 10 in a thickness direction.

The first opening 15 is defined by a border 15a (fifth border), a border 15b (first border), and a border 15c (second border). The border 15a curves so as to project towards the pressure-sensitive region 201a. The border 15b is connected to the border 17a among the pair of borders 17a and 17b, and extends substantially straight in a transverse direction. The border 15c is connected to the border 17b among the pair of borders 17a and 17b, and extends substantially straight in a lengthwise direction. Each of the borders 15b and 15c is longer than the diameter of the pressure-sensitive region 202b. Except for portions of the both ends, the border 15a is formed along a quarter-circle outline around the pressure-sensitive region 202b, the quarter-circle outline facing the pressure-sensitive region 201a.

A portion of each of the connections between the border 17a and the border 15b, and between the border 17b and the border 15c is curved so that the borders are smoothly connected. In other words, the portion of each of the connections between the border 15b and the border 17a, and between the border 15c and the border 17b is slightly curved. The borders, however, are not necessarily connected smoothly. In such a case, the borders 17a and 17b of the cut line 17, and the two borders 15b and 15c are respectively connected at an angle to each other. Further, the border 15b and the border 15a, and border 15c and the border 15a are respectively connected smoothly in a small radius of curvature.

The second opening 16 is defined by a border 16a (sixth border), a border 16b (third border) and a border 16c (fourth border). The border 16a is curved so as to project towards the pressure-sensitive region 202b. The border 16b is connected to the border 17b among the pair of borders 17a and 17b forming the cut line 17, and extends substantially straight in the transverse direction. The border 16c is connected to the border 17a among the pair of borders 17a and 17b forming the cut line 17, and extends substantially straight in the lengthwise direction. Each of the borders 16b and 16c is longer than the diameter of the pressure-sensitive region 201a. Except for portions of both ends, the border 16a is formed along a quarter-circle outline around the pressure-sensitive region 201a, the quarter-circle outline facing the pressure-sensitive region 202b.

A portion of each of the connections between the border 17a and the border 16c, and between the border 17b and the border 16b is curved so that the borders are smoothly connected. In other words, a portion of each of the connections between the border 16b and the border 17b, and between the border 16c and the border 17a is slightly curved. The borders, however, are not necessarily connected smoothly. In such a case, the borders 17a and 17b of the cut line 17, and the two borders 16c and 16b are respectively connected at an angle to each other. Further, the border 16b and the border 16a, and border 16c and the border 16a are respectively connected smoothly in a small radius of curvature.

Each pressure-sensitive region is substantially surrounded by the upper-left first opening 15 and the lower-right second opening 16. Around the edges of the body pressure distribution sensor sheet 10 may be a pressure-sensitive region which is not paired with another pressure-sensitive region in the first oblique direction. Such a pressure-sensitive region is also substantially surrounded by the upper left first opening 15 and the lower right second opening 16.

The cut line 17 extends in the first oblique direction, and is formed with the two borders 17a and 17b in the first oblique direction. The cut line 17 has a predetermined width in a second oblique direction perpendicular to the first oblique direction, which separates the two borders 17a and 17b. The predetermined width is shorter than the diameter of the pressure-sensitive region 202b. As described above, the border 17a of the cut line 17 is connected to the border 15b of the first opening 15 and the border 16c of the second opening 16. Meanwhile, the border 17b of the cut line 17 is connected to the border 15c of the first opening 15 and the border 16b of the second opening 16. The first opening 15 and the second opening 16 are thus connected to the cut line 17, forming a substantially x-shaped opening defined by an outline 19 (see FIG. 11(c)).

Thus, a first opening 15 and a second opening 16 are provided to each of the vicinities of the pressure-sensitive regions 201a to 201d, 202a to 202d, 203a to 203d, and 204a to 204d on the entire surface of the body pressure distribution sensor sheet 10. Further on the body pressure distribution sensor sheet 10, the first opening 15 of one pressure-sensitive region and the second opening 16 of another pressure-sensitive region are connected by the cut line 17, the one pressure-sensitive region and the another pressure-sensitive region being adjacent to each other in the first oblique direction. As a result, as illustrated in FIG. 2, each of the cut lines 17 is formed in the first oblique direction, and all of the cut lines 17 are arranged parallel to each other on the entire surface of the body pressure distribution sensor sheet 10.

The body pressure distribution sensor sheet 10 has first openings 15, second openings 16, and cut lines 17 formed thereon in such a pattern as illustrated in FIG. 5.

In the present embodiment, 10 μm-thick transparent PET (polyethylene terephthalate) is adapted as a material of the first sheet 11 and the second sheet 12. The material of the first sheet 11 and the second sheet 12, however, is not limited to this: Polyester or polyimide may be employed.

The following describes wires on the body pressure distribution sensor sheet 10 next. Taking the pressure-sensitive region 202 as an example, the electrode 32a included in the pressure-sensitive region 202a on the first sheet 11 is connected to other electrodes respectively included in pressure-sensitive regions 202b, 202c, and 202d on the first sheet 11 by a column wire 22 on the first sheet 11. Further, the electrode 42a included in the pressure-sensitive region 202a on the second sheet 12 is connected to other electrodes respectively included in pressure-sensitive regions 201a, 203a, and 204a on the second sheet 12 by a row wire 25 on the second sheet 12. Likewise, column wires connect electrodes on the first sheet 11 and row wires connect electrodes on the second sheet 12 for other pressure-sensitive regions.

The first openings 15, the second openings 16, and the cut lines 17 are formed around the pressure-sensitive regions so as not to intersect with wires 21 to 28. One end of the each of the wires 21 to 28 is at an edge of the body pressure distribution sensor sheet 10. The wires 21 to 28 are respectively provided with terminals 21t and 28t at the one end. The terminals 21t and 28t are for connecting the wires 21 to 28 to the sensor connector 80, respectively.

Although the pressure-sensitive regions 201a to 201d, 202a to 202d, 203a to 203d and 204a to 204d, and wires 21 to 28 are shielded by the second sheet 12, these pressure-sensitive regions and wires are seen through because the second sheet 12 is made of transparent PET. Thus, the pressure-sensitive regions 201a to 201d, 202a to 202d, 203a to 203d and 204a to 204d, and wires 21 to 28 are illustrated with solid lines in FIG. 2.

Figure 9:
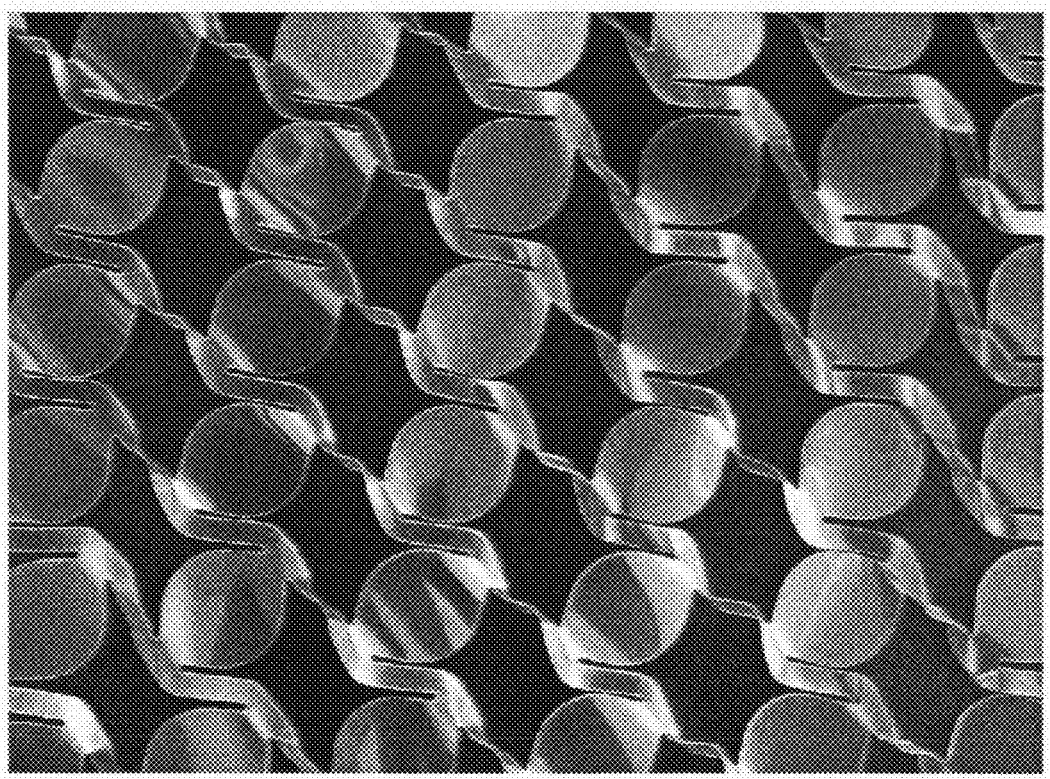
FIG. 9 illustrates a PET sheet stretched in a transverse direction, the PET sheet having formed thereon first and second openings and cut lines in the same pattern as the body pressure distribution sensor sheet of FIG. 1.
Figure 10:
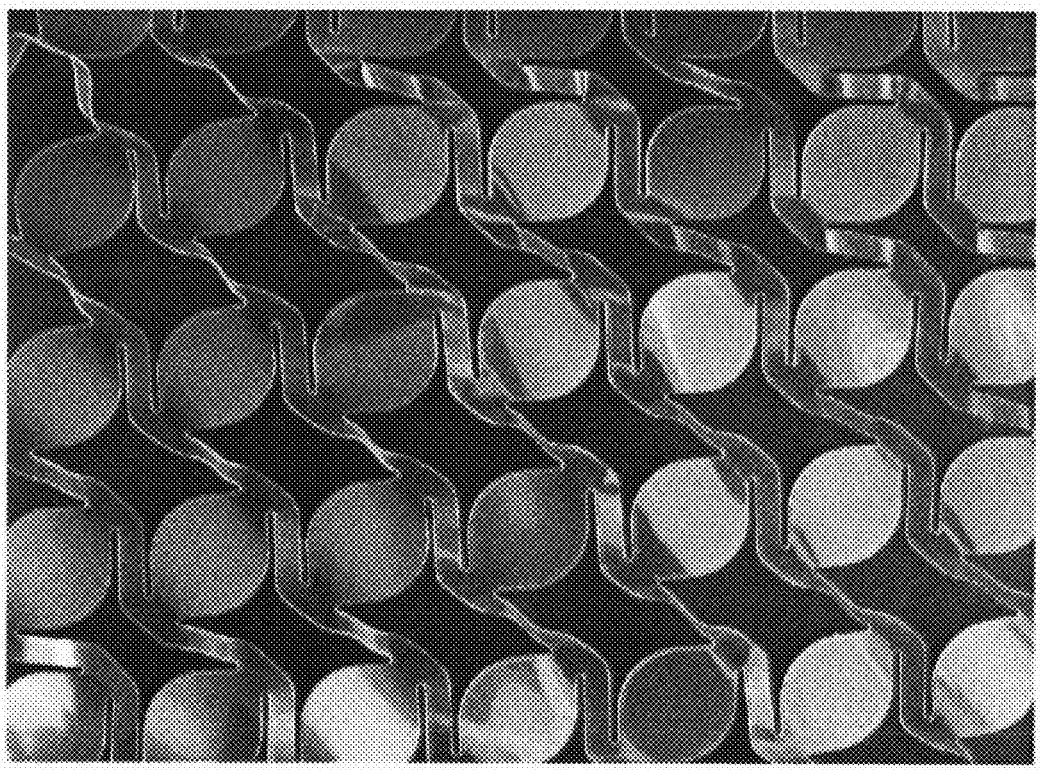
FIG. 10 illustrates the PET sheet of FIG. 9 stretched in a lengthwise direction.

The following describes stretchability of the body pressure distribution sensor sheet. FIG. 6 is a schematic view describing stretchability of the body pressure distribution sensor sheet 10 of FIG. 1. FIG. 9 illustrates a PET sheet stretched in a transverse direction, which PET sheet having formed thereon first and second openings and cut lines in the same pattern as the body pressure distribution sensor sheet 10 of FIG. 1. FIG. 10 illustrates the PET sheet of FIG. 9 stretched in a lengthwise direction.

When the body pressure distribution sensor sheet 10 having the first openings 15, the second openings 16, and the cut lines 17 thereon is pulled in the transverse direction as illustrated in FIG. 6(a), the body pressure distribution sensor sheet 10 as a whole significantly stretches in the transverse direction while transforming the surface three-dimensionally with the first openings 15, the second openings 16 and the cut lines 17. Here, FIG. 9 illustrates a PET sheet stretched in the transverse direction, the PET sheet having thereon the first and second openings and cut lines in the same pattern as the body pressure distribution sensor sheet 10. Note that the body pressure distribution sensor sheet 10 deforms in the same manner when stretching in the transverse direction.

When the body pressure distribution sensor sheet 10 is pulled in the lengthwise direction as illustrated in FIG. 6(*b*), the body pressure distribution sensor sheet 10 as a whole significantly stretches in the lengthwise direction while transforming the surface three-dimensionally with the first openings 15, the second openings 16 and the cut lines 17. Here, FIG. 10 illustrates the PET sheet having the same cut lines as the body pressure distribution sensor sheet 10 stretched in the lengthwise direction. Note that the body pressure distribution sensor sheet 10 deforms in the same manner when stretching in the lengthwise direction.

As described above, the body pressure distribution sensor sheet 10 has a combination of an excellent stretchability in the transverse direction as illustrated in FIG. 6(*a*), and an excellent stretchability in the lengthwise direction as illustrated in FIG. 6(*b*). The lengthwise and transverse directions here are the same directions as the lengthwise and transverse directions in FIG. 2, respectively.

The following describes a procedure for measurement of body pressure distribution on a patient with the body pressure distribution measurement system 1 employing the body pressure distribution sensor sheet 10, the patient lying on the body pressure distribution sensor sheet 10 disposed on the bed 90.

First, a body pressure distribution measurement software program (not illustrated) previously installed in the PC 100 is activated by operating the PC 100 with the keyboard 110 or the mouse 120. When the software program is given an instruction to read out data, a voltage is sequentially impressed to the column wires 21 to 24 by order of the PC 100, allowing a voltage in the row wires 25 to 28 to be detected for each column wire in the sensor connector 80 connected to the body pressure distribution sensor sheet 10.

Body pressure distribution is calculated from measurement of a change in resistivity for each pressure-sensitive resistor of the body pressure distribution sensor sheet 10 as described above. Here, the sensor connector 80 has built-in pins corresponding to the terminals 21*t* to 28*t* of the body pressure distribution sensor sheet 10, which enable the sensor connector 80 to communicate an electric signal with the distribution sensor sheet 10. Further, the sensor connector 80 has a built-in multiplexer which combines separately inputted signals into one, and an A/D converter. The multiplexer and the A/D converter enable the sensor connector 80 to convert an electric signal which is analog data received from the body pressure distribution sensor sheet 10 into a digital signal. The sensor connector 80 then transmits the digital signal to the PC 100.

Thus, the electric signal of pressure distribution measurement data transferred to the PC 100 from the sensor connector 80 is read into the PC 100.

As illustrated above, the body pressure distribution measurement software program in the PC 100 carries out a proper calculation for measured resistivity of each pressure-sensitive region. A body pressure distribution measurement result is then displayed on the display 70. Here, body pressure distribution on a patient is illustrated by the following methods, for example. One method is to two-dimensionally display an image representing the entire body pressure distribution sensor sheet 10 to display different colors according to the magnitude of pressure applied to each of the pressure-sensitive resistors. Another method is to three-dimensionally display an image representing the entire body pressure distribution sensor sheet 10 with rise and fall according to the magnitude of pressure applied to each of the pressure-sensitive resistors. Further, the load center, contact area, total load value or the like may be displayed as a graph or a table. The body pressure distribution on the patient's body applied on the body pressure distribution sensor sheet 10 is thus visually confirmed with the information displayed on the display 70.

Figure 7:
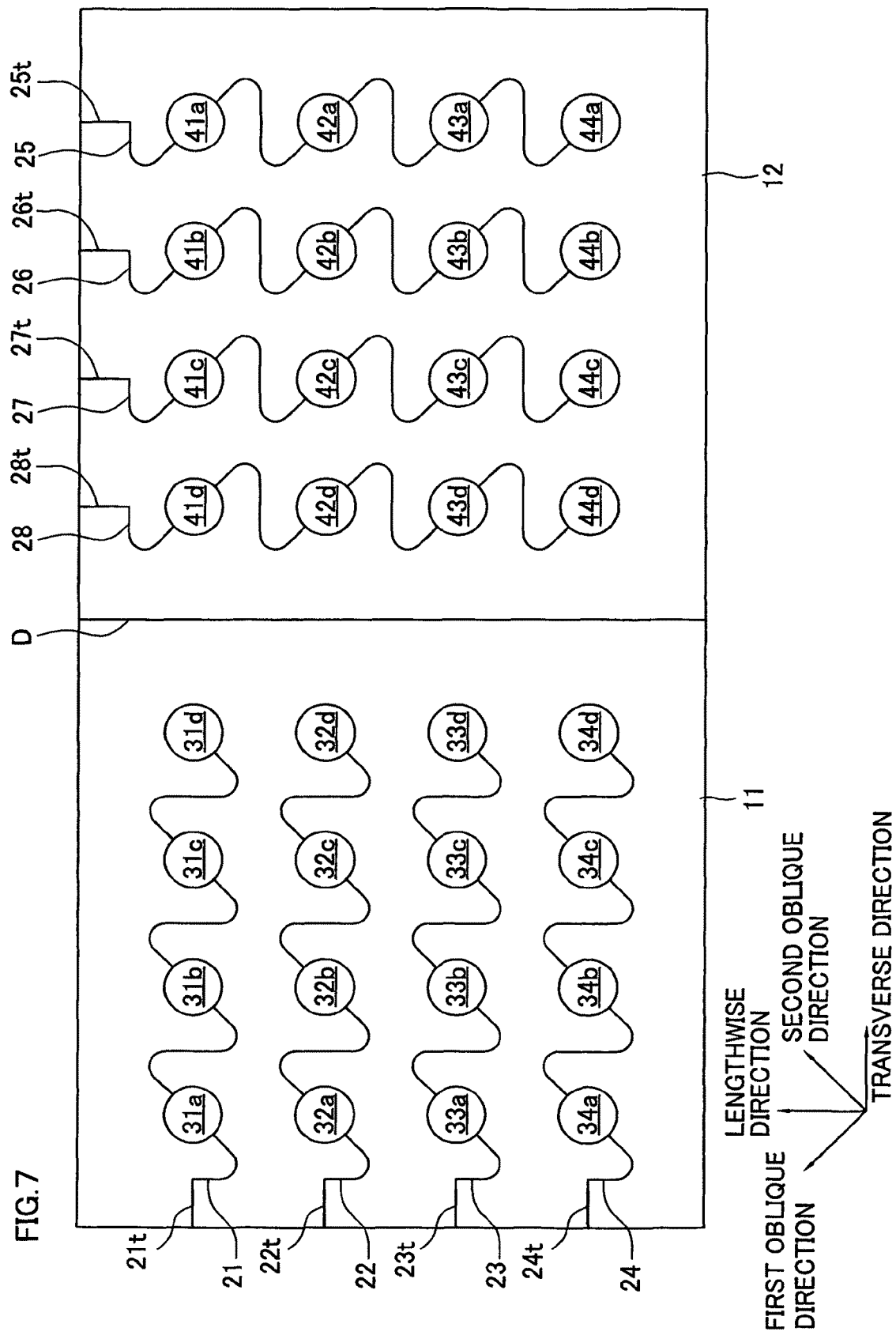
FIG. 7 illustrates first and second sheets with electrodes and wires formed thereon.
Figure 8:
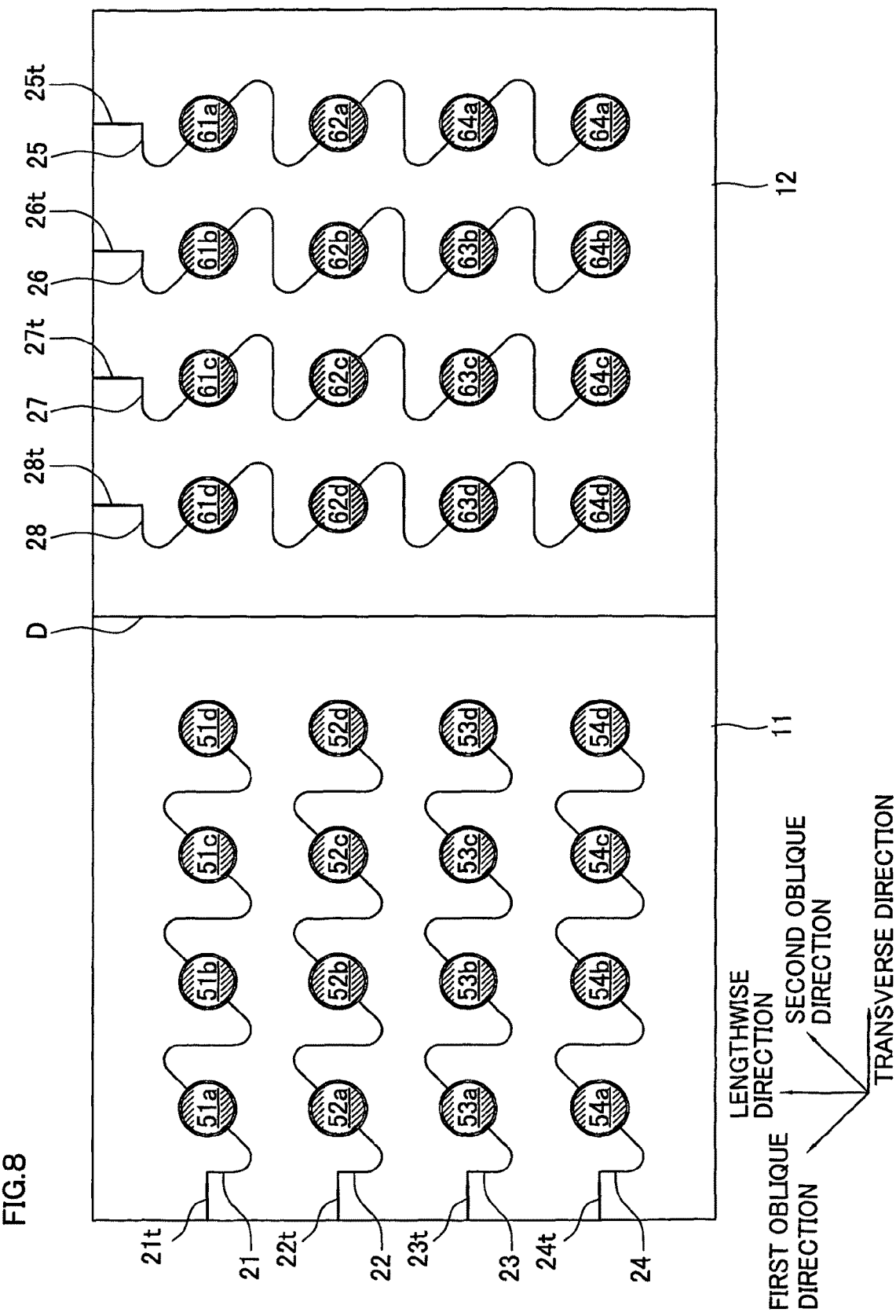
FIG. 8 illustrates the electrodes of FIG. 7 with pressure-sensitive resistors laminated thereon.

The following describes a production method of the body pressure distribution sensor sheet 10 shown in FIG. 2, with further reference to FIGS. 7 and 8. FIG. 7 illustrates the first sheet 11 and the second sheet 12 with electrodes and wires formed thereon. FIG. 8 illustrates the electrodes of FIG. 7 with pressure-sensitive resistors laminated thereon.

First, a plurality of plane circular electrodes 31*a* to 31*d*, 32*a* to 32*d*, 33*a* to 33*d* and 34 to 34*d*, and four column wires 21 to 24 are formed on the first sheet 11, as illustrated in FIG. 7. Each of the electrodes 31*a* to 31*d*, 32*a* to 32*d*, 33*a* to 33*d* and 34 to 34*d* is silver paste printed on the first sheet 11. Further, the column wires 21 to 24 are vertically aligned four wires. Each of the column wires 21 to 24 is silver paste printed and extended in a horizontal orientation in such a pattern as illustrated in FIG. 7 on the first sheet 11.

Further, a plurality of plane circular electrodes 41*a* to 41*d*, 42*a* to 42*d*, 43*a* to 43*d* and 44*a* to 44*d*, and four wires 25 to 28 are formed on the second sheet 12. Each of the electrodes 41*a* to 41*d*, 42*a* to 42*d*, 43*a* to 43*d* and 44*a* to 44*d* is silver paste printed on the second sheet 12. Further, the row wires 25 to 28 are horizontally aligned four wires. Each of the row wires 25 to 28 is silver paste printed and extended in a vertical orientation in such a pattern as illustrated in FIG. 7 on the second sheet 12. Furthermore, each of the wires 21 to 28 has a triangular-wave-type shape as illustrated in FIG. 7, so as to avoid intersecting with the first openings 15, the second openings 16 and cut lines 17.

Next, the circular pressure-sensitive resistors 51*a* to 51*d*, 52*a* to 52*d*, 53*a* to 53*d*, and 54*a* to 54*d* are respectively laminated onto the electrodes 31*a* to 31*d*, 32*a* to 32*d*, 33*a* to 33*d* and 34 to 34*d* on the first sheet 11, as illustrated in FIG. 8. Likewise, the circular pressure-sensitive resistors 61*a* to 61*d*, 62*a* to 62*d*, 63*a* to 63*d*, and 64*a* to 64*d* are respectively laminated onto the electrodes 41*a* to 41*d*, 42*a* to 42*d*, 43*a* to 43*d* and 44*a* to 44*d* on the second sheet 12. These pressure-sensitive resistors 51*a* to 51*d*, 52*a* to 52*d*, 53*a* to 53*d*, 54*a* to 54*d*, 61*a* to 61*d*, 62*a* to 62*d*, 63*a* to 63*d*, and 64*a* to 64*d* are arranged so that when the first sheet 11 and the second sheet 12 are folded along the folding line D illustrated in FIGS. 7 and 8, the pressure sensitive resistors at symmetrical positions with respect to the folding line D contact one another. The pressure-sensitive resistor 51*a* of the first sheet 11 and the pressure-sensitive resistor 61*a* of the second sheet 12, for example, are in an axisymmetric relation, and thus are arranged so as to contact each other when the first sheet 11 and the second sheet 12 are folded along the folding line D. Other pressure-sensitive resistors also are arranged so that two pressure-sensitive resistors respectively provided to the first sheet 11 and the second sheet 12 overlap with one another when the first sheet 11 and the second sheet 12 are folded along the folding line D as well.

With the above structures of the first sheet 11 and the second sheet 12, each of a pair of corresponding electrodes respectively provided on the first sheet 11 and the second sheet 12 is connected with another electrode by a wire forming such a pattern as illustrated in FIG. 7.

The first sheet 11 and the second sheet 12 are laminated with the folding line D illustrated in FIG. 8 as an axis so that a surface of the first sheet 11 and a surface of the second sheet 12 contact one another, the surface of the first sheet 11 having thereon the pressure-sensitive resistors 51a to 51d, 52a to 52d, 53a to 53d, 54a to 54d, and the surface of the second sheet 12 having thereon the pressure-sensitive resistors 61a to 61d, 62a to 62d, 63a to 63d, and 64a to 64d. Here, an adhesive layer 150 and an insulation layer 160 interpose between parts of the first sheet 11 and the second sheet 12 except for the pressure-sensitive resistors (see FIG. 3). The adhesive layer 150 is made of an adhesive for adhering the first sheet 11 and the second sheet 12. The insulation layer 160 is for preventing the wires 21 to 24 and the wires 25 to 28 from contacting.

Forming the first openings 15, the second openings 16, and the cut lines 17 on the laminated first sheet and second sheet 12 produces the body pressure distribution sensor sheet 10 illustrated in FIG. 2.

Figure 12:
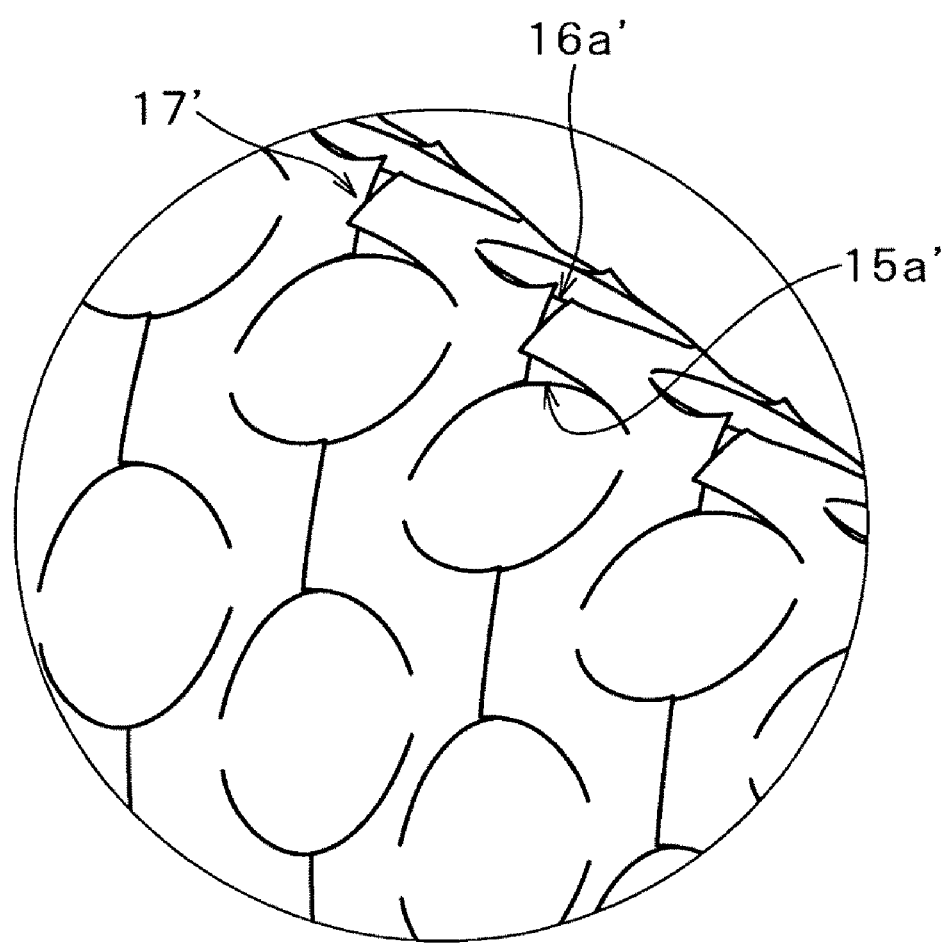
FIG. 12 is a partial perspective view illustrating a bent sheet on which cut lines same as the basic shape lines of FIG. 11 are formed.
Figure 13:
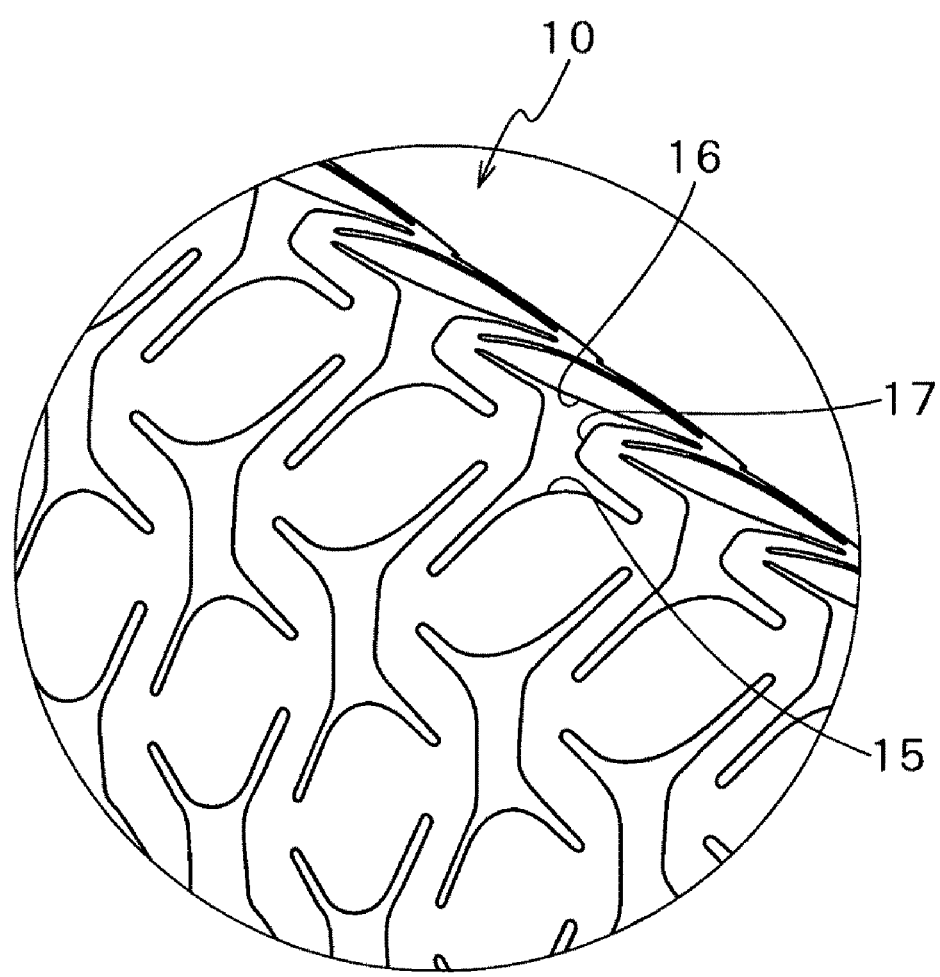
FIG. 13 is a partial perspective view illustrating the pressure distribution sensor sheet of FIG. 2 when bent.

The following describes a method for forming the first openings 15, the second openings 16, and cut lines 17. FIG. 11 illustrates the method for forming the first and second openings and the cut lines of the body pressure distribution sensor sheet in sequence of processes. FIG. 12 is a partial perspective view illustrating the sheet illustrated in FIG. 11 when bent, the sheet having cut lines same as the basic shape lines are formed. FIG. 13 is a partial perspective view illustrating the pressure distribution sensor sheet 10 of FIG. 2 when bent.

When forming a first opening 15, a second opening 16, and a cut line 17 on the body pressure distribution sensor sheet 10, basic shape lines 15a', 16a', and 17' respectively corresponding to the first opening 15, the second opening 16, and the cut line 17 are imagined first, as illustrated in FIG. 11(a). The basic shape lines 15a' and 16' respectively correspond to the openings 15 and 16. The basic shape lines 17' connects a center portion of the basic shape line 15' and a center portion of the basic shape line 16'.

If cut lines substantially the same as the basic shape lines 15a' to 17' (i.e., linear cut lines with little width) are formed on the body pressure distribution sensor sheet, vicinities of the corners, i.e., connections between the basic shape lines 15a' and 17' and between the basic shape lines 16a' and 17' (hatched areas of FIG. 11(a)) partly project from the surface of the sensor sheet as illustrated in FIG. 12 when the body pressure distribution sensor sheet is folded along a folding line E crossing the centers of the cut lines 17' aligned in the transverse direction. If the vicinities of the corners project from the surface, when a patient lies on the body pressure distribution sensor sheet disposed on a flexible support and thus the body pressure distribution sensor sheet is deformed to bend, the vicinities of the corners partly projected from the surface of the sensor sheet come in contact with the patient. This contact force affects the pressure-sensitive resistors, possibly preventing proper measurement of body pressure distribution on the patient.

Furthermore, not only the basic shape lines 15a' to 17', but also imaginary straight lines 15b', 15c', 16b', and 16c' are imagined, as illustrated in FIG. 11(b). The imaginary straight lines 15b' and 15c' extend from both ends of the basic shape line 15a' to the basic shape line 17' in the transverse and the lengthwise directions, respectively. The imaginary straight lines 16b' and 16c' extend from both ends of the basic shape line 16a' to the basic shape line 17' in the transverse and lengthwise directions, respectively. The imaginary straight lines 15b' and 15c' respectively correspond to the borders 15b and 15c of the first opening 15. The imaginary straight lines 16b' and 16c' respectively correspond to the borders 16b and 16c of the second opening 16. When the region surrounded by the three lines 15a', 15b', and 15c' is removed, the corner of the connection between the basic shape lines 15a' and 17' is removed. When the region surrounded by the three lines 16a', 16b' and 16c' is removed, the corner of the connection between the basic shape lines 16a' and 17' is removed. In other words, the first openings 15 and the second openings 16 eliminate corners which partly project from the surface of the sensor sheet when the sensor sheet is folded along the folding line E. This allows proper measurement of pressure distribution even when the pressure distribution sensor sheet 10 is deformed to bend.

Next, imaginary straight lines 17a' and 17b' are imagined. The imaginary straight lines 17a' and 17b' are parallel to the basic shape line 17', and each of the imaginary straight lines 17a' and 17b' is equally distanced from the basic shape line 17'. The imaginary straight lines 17a' and 17b' respectively correspond to the borders 17a and 17b of the cut line 17. Then, a process is carried out to smooth the connections among the basic shape lines 15a', 16a' and 17', and imaginary straight lines 15b', 15c', 16b', 16c', 17a', and 17b', as illustrated in FIG. 11(c). Thus, the outline 19 of the first opening 15, the second opening 16, and the cut line 17 is defined.

Next, an opening along the outline 19 is formed on the pressure distribution sensor sheet 10 by laser beam machining or pressing. Thus, the first opening 15, the second opening 16, and the cut line 17 are formed on the pressure distribution sensor sheet 10. Thus, even when the pressure distribution sensor sheet 10 is folded along the same position as the folding line E illustrated in FIG. 11(a), the corners barely project from the surface of the sensor sheet since the corners have been already removed, as illustrated in FIG. 13. In other words, the first opening 15 is defined by three borders including the borders 15b and 15c, and the second opening 16 is defined by three borders including the borders 16b and 16c. Thus, the corners indicated by hatching in FIG. 11(a) are properly chamfered. With the chamfered corners, the vicinities of the openings 15 and 16, and cut lines 17 is less likely to partly protrude significantly from the surface when the pressure distribution sensor sheet 10 is bent in one of the lengthwise and transverse directions. Thus, pressure distribution is properly measured even when the pressure distribution sensor sheet 10 is deformed to bend.

The first openings 15, the second openings 16, and the cut lines 17 on the pressure distribution sensor sheet 10 give the pressure sensor sheet 10 stretchability in both lengthwise and transverse directions. This allows the pressure distribution sensor sheet 10 to deform while conforming to unevenness of the surface of the support even when disposed on a flexible support such as a mattress or futon mattress. Thus, measurement of pressure distribution such as body pressure distribution on a patient is properly carried out.

Further, the total length of the lengths of the outlines of the first opening 15 and the second opening 16 and the length of the cut line 17 (length of outline in the present embodiment) is shorter than a length of a spiral cut line. Thus, the first opening 15, the second opening 16, and the cut line 17 are speedily formed at a low cost.

The first opening 15 is defined by the borders 15b and 15c, and the curved border 15a. The second opening 16 is defined by the borders 16b and 16c, and the curved border 16a. Thus, stretchability of the sensor sheet 10 in lengthwise and transverse directions is improved with a simple structure. Further, each of the electrodes 31a to 31d, 32a to 32d, 33a to 33d, 34a to 34d, 41a to 41d, 42a to 42d, 43a to 43d, and 44a to 44d is circular. The border 15a is formed along a quarter-circle outline formed around the pressure-sensitive region 202b, the quarter-circle outline facing the pressure sensitive region 201a. The border 16a is formed along a quarter-circle outline around the pressure-sensitive region 201a, the quarter-circle outline facing the pressure sensitive region 202b. Thus, the stretchability of sensor sheet in lengthwise and transverse directions is improved while preventing the openings from intersecting one another. In addition, the cut line 17 is formed between a center portion of the first opening 15 and a center portion of the second opening 16. This equalizes the stretchability in the lengthwise direction and the transverse direction.

Further, the pair of borders 17a and 17b of the cut line 17 are apart from each other. This prevents the pair of borders 17a and 17b constituting the cut line 17 from contacting each other even when the sensor sheet 10 is deformed to bend in the first oblique direction. This prevents the pair of borders 17a and 17b from contacting one another to interfere one another, thus allowing proper pressure distribution measurement.

Further, the wires 21 to 28 are formed avoiding all the first openings 15, the second openings 16 and the cut lines 17. This allows measurement of pressure distribution without losing the stretchability of the body pressure distribution sensor sheet 10 in the lengthwise and transverse directions.

In addition, the borders 15b and 15c are smoothly connected to the borders 17a and 17b, respectively. The borders 16b and 16c are smoothly connected to the borders 17a and 17b, respectively. Thus, vicinities of the connections between the first opening 15 and the cut line 17, and between the second opening 16 and the cut line 17 are less likely to partly project from the surface of the sensor sheet when the sensor sheet 10 is bent in either the lengthwise or transverse direction. This allows proper measurement of pressure distribution even when the pressure distribution sensor sheet 10 is deformed to bend.

A preferred embodiment of the present invention has been described above. However, the present invention is not limited to the above-described embodiment. Various changes can be made within the scope of the invention. The shapes of the first opening 15 and the second opening 16 of the body pressure distribution sensor sheet 10, for instance, is one example, and thus the shapes are not limited to this. A small circular hole may be formed to an end of each of the openings 15 and 16 in the second oblique direction. In such a case, the circular holes prevents the sheet from tearing even when the body pressure distribution sensor sheet expands in the lengthwise direction, the transverse direction, or an oblique direction. Further, the cut line 17 may be a linear cut line where the borders 17a and 17b contact one another. The cut line 17 is not required to linearly connect the center portion of the first opening 15 and the center portion of the second opening 16. Furthermore, each of the borders 15a and the 16a is not necessarily formed along a quarter-circle outline facing an electrode. Nor does each of the borders 15a and 16a necessarily have to project towards pressure-sensitive regions adjacent to each other in the first oblique direction.

The above embodiment describes a body pressure distribution sensor sheet 10 having sixteen electrodes of four columns and four rows; however, this is merely an example. The number of electrodes is changeable.

Further, an electrode is circular in the above embodiment; however, the shape of the electrode is not limited to this. The shape of the electrode may be polygon, for example.

Further, pressure-sensitive conductive ink is employed for a pressure-sensitive resistor in the above embodiment. However, the material does not necessarily have to be pressure-sensitive conductive ink, as long as electric resistance of the material is changed according to pressure, such as pressure-sensitive conductive rubber.

Further, the electrodes are printed silver paste in the above embodiment; however, the material is not limited to silver paste as long as it is conductive ink. Further, the electrodes may be photo etched which does not require the electrodes to be printed.

Further, a pressure-sensitive resistor may be provided on each of the electrodes of the first sheet and the second sheet 12. However, a pressure-sensitive resistor may be provided on each of the electrodes of only one of the first sheet 11 and the second sheet 12.

The invention claimed is:

1. A sensor sheet comprising:
   a first sheet having thereon a plurality of electrodes arranged apart from each other in a lengthwise direction and a transverse direction to form a matrix;
   a second sheet which is laminated on the first sheet, and has thereon a plurality of electrodes arranged apart from each other in the two directions to form a matrix, the electrodes respectively facing the electrodes of the first sheet; and
   a plurality of pressure-sensitive resistors each arranged between one of the electrodes on the first sheet and one of the electrodes on the second sheet;
   wherein a first opening, a second opening, and a cut line are formed between each pair of electrodes adjacent to each other in one oblique direction between the lengthwise direction and the transverse direction: the first opening being formed between the pair of electrodes, and near a first electrode of the pair of electrodes; the second opening being formed between the first opening and a second electrode of the pair of electrode, and near the second electrode; and the cut line being formed with a pair of borders extending in the one oblique direction, and connecting the first opening and the second opening, and
   wherein the first opening is defined by a plurality of borders including a first border and a second border, the first border being connected to a first one of the pair of borders of the cut line and extending in the transverse direction, and the second border being connected to a second one of the pair of borders of the cut line, and extending in the lengthwise direction, and
   the second opening is defined by a plurality of borders including a third border and a fourth border, the third border being connected to the second one of the pair of borders of the cut line and extending in the transverse direction, and the fourth border being connected to the first one of the pair of borders of the cut line and extending in the lengthwise direction.

2. The sensor sheet according to claim 1, wherein the first opening is defined by the first border, the second border, and a fifth border which curves to project towards the second electrode,
   and the second opening is defined by the third border, the fourth border, and a sixth border which curves to project towards the first electrode.

3. The sensor sheet according to claim 2, wherein each of the electrodes is circular,
   and wherein the fifth border has a portion formed along a quarter-circle outline around the first electrode, the quarter-circle outline facing the second electrode, and the sixth border has a portion formed along a quarter-circle outline around the second electrode, the quarter-circle outline facing the first electrode.

4. The sensor sheet according to claim 1, wherein the cut line is formed between a center portion of the first opening and a center portion of the second opening.

5. The sensor sheet according to claim 1, wherein the pair of borders of the cut line are apart from each other.

6. The sensor sheet according to claim 1, wherein the first sheet has thereon a wire connecting the electrodes formed on the first sheet, and the second sheet has thereon a wire connecting the electrodes formed on the second sheet,
and wherein both of the wires on the first sheet and the second sheet are provided avoiding the first opening, the second opening, and the cut line.

7. The sensor sheet according to claim 1, wherein the first border and the first one of the pair of borders of the cut line are smoothly connected, the second border and the second one of the pair of borders of the cut line are smoothly connected, the third border and the second one of the pair of borders of the cut line are smoothly connected, and the fourth border and the first one of the pair of borders of the cut line are smoothly connected.

* * * * *